United States Patent
Davis et al.

(10) Patent No.: US 10,421,786 B2
(45) Date of Patent: Sep. 24, 2019

(54) PEPTIDES THAT TARGET INFLAMED OR DISTRESSED CARDIAC TISSUE AND USES RELATED THERETO

(71) Applicant: Emory University, Atlanta, GA (US)

(72) Inventors: Michael Davis, Atlanta, GA (US); Mario Martinez, Atlanta, GA (US)

(73) Assignees: Emory University, Atlanta, GA (US); Children's Healthcare of Atlanta, Inc., Atlanta, GA (US)

(*) Notice: Subject to any disclaimer, the term of this patent is extended or adjusted under 35 U.S.C. 154(b) by 0 days.

(21) Appl. No.: 16/012,306

(22) Filed: Jun. 19, 2018

(65) Prior Publication Data
US 2018/0362584 A1    Dec. 20, 2018

Related U.S. Application Data

(60) Provisional application No. 62/521,636, filed on Jun. 19, 2017.

(51) Int. Cl.
| | | |
|---|---|---|
| C07K 7/08 | (2006.01) | |
| A61K 47/54 | (2017.01) | |
| A61K 47/60 | (2017.01) | |
| A61K 49/18 | (2006.01) | |
| A61K 49/14 | (2006.01) | |
| A61K 47/64 | (2017.01) | |
| A61K 49/00 | (2006.01) | |
| C07K 17/14 | (2006.01) | |
| G01N 33/58 | (2006.01) | |
| A61K 38/00 | (2006.01) | |

(52) U.S. Cl.
CPC .............. *C07K 7/08* (2013.01); *A61K 47/542* (2017.08); *A61K 47/60* (2017.08); *A61K 47/64* (2017.08); *A61K 49/0032* (2013.01); *A61K 49/0056* (2013.01); *A61K 49/14* (2013.01); *A61K 49/1821* (2013.01); *C07K 17/14* (2013.01); *G01N 33/582* (2013.01); *A61K 38/00* (2013.01); *G01N 2800/32* (2013.01)

(58) Field of Classification Search
CPC ...... A61K 38/00; A61K 47/542; A61K 47/60; A61K 47/64; A61K 49/0032; A61K 49/0056; A61K 49/14; A61K 49/1821; C07K 7/08
See application file for complete search history.

(56) References Cited

U.S. PATENT DOCUMENTS

| | | | |
|---|---|---|---|
| 6,664,272 | B2 | 12/2003 | Snyder |
| 7,005,256 | B1 | 2/2006 | Tully |
| 7,358,049 | B2 | 4/2008 | Tully |
| 7,371,766 | B2 | 5/2008 | Snyder |
| 7,842,705 | B2 | 11/2010 | Snyder |
| 7,867,476 | B2 | 1/2011 | Knowlton |
| 8,252,846 | B2 | 8/2012 | Murthy |
| 9,585,915 | B2 | 3/2017 | Davis |
| 9,840,693 | B2 | 12/2017 | Davis |
| 2013/0203622 | A1 | 8/2013 | Hare |
| 2013/0332133 | A1* | 12/2013 | Horn ................... C12N 9/00 703/11 |
| 2014/0271694 | A1 | 9/2014 | Lipes |

OTHER PUBLICATIONS

Encyclopaedia Britannica, editors. Zygote. https://www.britannica.com/science/zygote, accessed online on Oct. 29, 2018, 2 pages. (Year: 2018).*
Bazan et al., Phage display—A powerful technique for immunotherapy, Hum Vaccin Immunother,2012, 8(12): 1817-1828.
Bonner et al., Monocyte imaging after myocardial infarction with 19F MRI at 3T: a pilot study in explanted porcine hearts, Eur Heart J Cardiovasc Imaging, 2015, 16(6):612-20.
Feldman et al. Myocarditis. N Engl J Med, 2000, 343(19):1388-98.
Gale et al. Noninvasive Imaging of Early Venous Thrombosis by 19F Magnetic Resonance Imaging With Targeted Perfluorocarbon Nanoemulsions, Circulation, 2015, 131(16):1405-14.
Hernandez et al., Synthesis of N-[Tris(hydroxymethyl)methyl]benzenecarboxamides: A Convenient Route to Polyhydroxylated Dendritic Cores, J Org Chem, 1999, 64(18):6905-6906.
Kircher et al., Novel Noninvasive Nuclear Medicine Imaging Techniques for Cardiac Inflammation, Curr Cardiovasc Imaging Rep, 2017, 10(2):6.
Kolodziej et al., Peptide optimization and conjugation strategies in the development of molecularly targeted magnetic resonance imaging contrast agents, Methods Mol Biol, 2014, 1088:185-211.
Lee et al., Noninvasive Imaging of Myocardial Inflammation in Myocarditis using 68Ga-tagged Mannosylated Human Serum Albumin Positron Emission Tomography, Theranostics, 2017, 7(2):413-424.
Liu et al., Screening specific polypeptides of breast cancer stem cells from a phage display random peptide library, Oncol Lett, 2016, 12(6):4727-4731.
Mandelin et al., Selection and identification of ligand peptides targeting a model of castrate-resistant osteogenic prostate cancer and their receptors., Proc Natl Acad Sci U S A. 2015, 112(12):3776-81.
Martinez et al. Identification of targeting peptides for the diagnosis of myocarditis, Nanomedicine (Lond). 2018, 13 (7):787-801.

(Continued)

*Primary Examiner* — Marcela M Cordero Garcia
(74) *Attorney, Agent, or Firm* — Emory Patent Group

(57) ABSTRACT

This disclosure relates to peptides useful for targeting inflamed or distressed tissue and uses related thereto. In certain embodiment, the peptides comprise SEQ ID NO: 1-14, or variants or derivatives thereof. In certain embodiments, peptides disclosed herein are conjugated to a label to detect, measure, or image cardiac tissue useful in the diagnosis of myocarditis. In certain embodiments, the peptides are conjugated to a particle coating for use in ultrasound imaging, MRI, or targeted therapy. In certain embodiments, peptides disclosed herein are conjugated to a drug or a particle containing a drug useful for targeted therapy.

14 Claims, 2 Drawing Sheets
Specification includes a Sequence Listing.

(56) References Cited

OTHER PUBLICATIONS

Nemudraya et al., Phage Peptide Libraries As a Source of Targeted Ligands, Acta Naturae, 2016, 8(1): 48-57.
Temme et al. Noninvasive Imaging of Early Venous Thrombosis by 19F Magnetic Resonance Imaging With Targeted Perfluorocarbon Nanoemulsions, Circulation, 2015, 131:1405-1414.
Van Fieeswijk et al., Selective in vivo visualization of immune-cell infiltration in a mouse model of autoimmune myocarditis by fluorine-19 cardiac magnetic resonance, Circ Cardiovasc Imaging, 2013, 6(2):277-84.
Wang et al., 2A self-cleaving peptide-based multi-gene expression system in the silkworm Bombyx mori. Sci Rep, 2015, 5:16273.

* cited by examiner

| Peptide Name | Peptide Sequence |
|---|---|
| MyH-PhD-04 | LGDLHNRDNNSA (SEQ ID NO: 10) |
| MyH-PhD-05 | HSRTDYVQASYP (SEQ ID NO: 6) |
| MyH-PhD-09 | GLHTSATNLYLH (SEQ ID NO: 11) |
| MyH-PhD-13 | GDGNSVLKPGNW (SEQ ID NO: 12) |
| MyH-PhD-16 | TASDVPRSRPHS (SEQ ID NO: 13) |
| MyH-PhD-120 | SGVYKVAYDWQH (SEQ ID NO: 14) |

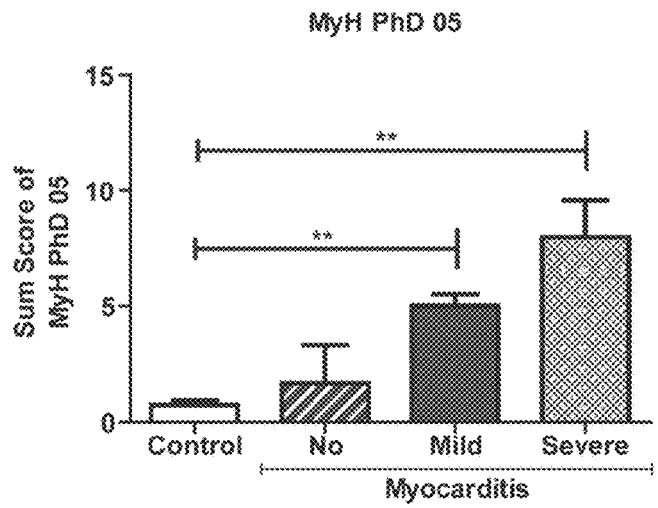

FIG. 3

```
DEFINITION   hypothetical protein [Frankia sp. EAN1pec].
ACCESSION    WP_020461938
VERSION      WP_020461938.1

Query   2    SRT-DYVQASYP   12         (SEQ ID NO: 4)
             SRT DYVQ SYP
Sbjct 408    SRTNDYVQDSYP  419         (SEQ ID NO: 7)
```

FIG. 4A

```
DEFINITION   aminotransferase apoenzyme [uncultured archaeon A07HN63].
ACCESSION    ESS08305
VERSION      ESS08305.1

Query   2    SRTDYVQASYP   12          (SEQ ID NO: 4)
             SR  YVQASYP
Sbjct  57    SRVTYVQASYP   67          (SEQ ID NO: 8)
```

FIG. 4B

```
DEFINITION   hypothetical protein TSUD_274540 [Trifolium subterraneum].
ACCESSION    GAU36176
VERSION      GAU36176.1

Query   1    HSRTDYV-QAS   10          SEQ ID NO: 5
             HSRTDYV Q S
Sbjct 1125   HSRTDYVSQTS  1135         SEQ ID NO: 9
```

FIG. 4C

SEQUENCE LISTING

<160> NUMBER OF SEQ ID NOS: 14

<210> SEQ ID NO 1
<211> LENGTH: 8
<212> TYPE: PRT

```
<213> ORGANISM: Artificial
<220> FEATURE:
<223> OTHER INFORMATION: Synthetic construct

<400> SEQUENCE: 1

Asp Tyr Val Gln Ala Ser Tyr Pro
1               5

<210> SEQ ID NO 2
<211> LENGTH: 8
<212> TYPE: PRT
<213> ORGANISM: Artificial
<220> FEATURE:
<223> OTHER INFORMATION: Synthetic construct

<400> SEQUENCE: 2

His Ser Arg Thr Asp Tyr Val Gln
1               5

<210> SEQ ID NO 3
<211> LENGTH: 8
<212> TYPE: PRT
<213> ORGANISM: Artificial
<220> FEATURE:
<223> OTHER INFORMATION: Synthetic construct

<400> SEQUENCE: 3

Ser Arg Thr Asp Tyr Val Gln Ala
1               5

<210> SEQ ID NO 4
<211> LENGTH: 11
<212> TYPE: PRT
<213> ORGANISM: Artificial
<220> FEATURE:
<223> OTHER INFORMATION: Synthetic construct

<400> SEQUENCE: 4

Ser Arg Thr Asp Tyr Val Gln Ala Ser Tyr Pro
1               5                   10

<210> SEQ ID NO 5
<211> LENGTH: 10
<212> TYPE: PRT
<213> ORGANISM: Artificial
<220> FEATURE:
<223> OTHER INFORMATION: Synthetic construct

<400> SEQUENCE: 5

His Ser Arg Thr Asp Tyr Val Gln Ala Ser
1               5                   10

<210> SEQ ID NO 6
<211> LENGTH: 12
<212> TYPE: PRT
<213> ORGANISM: Artificial
<220> FEATURE:
<223> OTHER INFORMATION: Synthetic construct

<400> SEQUENCE: 6

His Ser Arg Thr Asp Tyr Val Gln Ala Ser Tyr Pro
1               5                   10

<210> SEQ ID NO 7
<211> LENGTH: 12
<212> TYPE: PRT
<213> ORGANISM: Artificial
```

```
<220> FEATURE:
<223> OTHER INFORMATION: Synthetic construct

<400> SEQUENCE: 7

Ser Arg Thr Asn Asp Tyr Val Gln Asp Ser Tyr Pro
1               5                   10

<210> SEQ ID NO 8
<211> LENGTH: 11
<212> TYPE: PRT
<213> ORGANISM: Artificial
<220> FEATURE:
<223> OTHER INFORMATION: Synthetic construct

<400> SEQUENCE: 8

Ser Arg Val Thr Tyr Val Gln Ala Ser Tyr Pro
1               5                   10

<210> SEQ ID NO 9
<211> LENGTH: 11
<212> TYPE: PRT
<213> ORGANISM: Artificial
<220> FEATURE:
<223> OTHER INFORMATION: Synthetic construct

<400> SEQUENCE: 9

His Ser Arg Thr Asp Tyr Val Ser Gln Thr Ser
1               5                   10

<210> SEQ ID NO 10
<211> LENGTH: 12
<212> TYPE: PRT
<213> ORGANISM: Artificial
<220> FEATURE:
<223> OTHER INFORMATION: Synthetic construct

<400> SEQUENCE: 10

Leu Gly Asp Leu His Asn Arg Asp Asn Asn Ser Ala
1               5                   10

<210> SEQ ID NO 11
<211> LENGTH: 12
<212> TYPE: PRT
<213> ORGANISM: Artificial
<220> FEATURE:
<223> OTHER INFORMATION: Synthetic construct

<400> SEQUENCE: 11

Gly Leu His Thr Ser Ala Thr Asn Leu Tyr Leu His
1               5                   10

<210> SEQ ID NO 12
<211> LENGTH: 12
<212> TYPE: PRT
<213> ORGANISM: Artificial
<220> FEATURE:
<223> OTHER INFORMATION: Synthetic construct

<400> SEQUENCE: 12

Gly Asp Gly Asn Ser Val Leu Lys Pro Gly Asn Trp
1               5                   10

<210> SEQ ID NO 13
<211> LENGTH: 12
<212> TYPE: PRT
<213> ORGANISM: Artificial
<220> FEATURE:
```

```
<223> OTHER INFORMATION: Synthetic construct

<400> SEQUENCE: 13

Thr Ala Ser Asp Val Pro Arg Ser Arg Pro His Ser
1               5                   10

<210> SEQ ID NO 14
<211> LENGTH: 12
<212> TYPE: PRT
<213> ORGANISM: Artificial
<220> FEATURE:
<223> OTHER INFORMATION: Synthetic construct

<400> SEQUENCE: 14

Ser Gly Val Tyr Lys Val Ala Tyr Asp Trp Gln His
1               5                   10
```

PEPTIDES THAT TARGET INFLAMED OR DISTRESSED CARDIAC TISSUE AND USES RELATED THERETO

CROSS-REFERENCE TO RELATED APPLICATIONS

This application claims the benefit of U.S. Provisional Application No. 62/521,636 filed Jun. 19, 2017. The entirety of this application is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 17126US_ST25.txt. The text file is 2 KB, was created on Jun. 19, 2018, and is being submitted electronically via EFS-Web.

BACKGROUND

Myocarditis refers to localized or diffuse inflammation of the myocardium. Myocarditis can lead to slowing hear beats and irregular rhythms. Myocarditis can be caused by a viral infection or can be the result of cardiotoxic agents (drugs, toxins, and alcohol), or autoimmune disease. Diagnosis by an invasive endomyocardial biopsy is only recommended in patients with evidence for heart failure. As such, it often goes undiagnosed. Thus, there is a need to identify improved methods of diagnosing myocarditis.

Van Heeswijk et al. report selective in vivo visualization of immune-cell infiltration in a mouse model of autoimmune myocarditis by fluorine-19 cardiac magnetic resonance (CMR). Circulation Cardiovascular Imaging. 2013, 6:277-84. Bonner et al. report monocyte imaging after myocardial infarction with $^{19}F$ MRI. Eur Heart J Cardiovasc Imaging. 2015, 16(6):612-20. Gale et al. report gadolinium-based MRI contrast agents. Pediatr Radiol. 2017, 47: 507. See also Temme et al. $^{19}F$ magnetic resonance imaging with targeted perfluorocarbon nanoemulsions. Circulation. 2015, 131: 1405-1414.

Kircher et al report positron emission tomography (PET) using the radiolabeled glucose analog $[^{18}F]$-2-deoxy-2-fluoro-d-glucose (FDG) is a diagnostic test for nuclear imaging of (cardiac) inflammation. Curr Cardiovasc Imaging Rep. 2017, 10(2):6.

Lee et al. report imaging of myocardial inflammation using $^{68}Ga$-tagged mannosylated human serum albumin positron emission tomography. Theranostics. 2017, 7(2): 413-424. See also Kolodziej et al. Methods Mol Biol. 2014, 1088:185-211.

References cited herein are not an admission of prior art.

SUMMARY

This disclosure relates to peptides useful for targeting inflamed or distressed tissue and uses related thereto. In certain embodiment, the peptides comprise SEQ ID NO: 1-14, or variants or derivatives thereof. In certain embodiments, peptides disclosed herein are conjugated to a label to detect, measure, or image cardiac tissue useful in the diagnosis of myocarditis. In certain embodiments, the peptides are conjugated to a particle coating for use in ultrasound imaging, MRI, or targeted therapy. In certain embodiments, peptides disclosed herein are conjugated to a drug or a particle containing a drug useful for targeted therapy.

In certain embodiments, the disclosure relates to an isolated peptide comprising SEQ ID NO: 1 (DYVQASYP), SEQ ID NO: 2 (HSRTDYVQ), SEQ ID NO: 3 (SRTDYVQA), SEQ ID NO: 4 (SRTDYVQASYP), SEQ ID NO: 5 (HSRTDYVQAS), SEQ ID NO: 6 (HSRTDYVQASYP), SEQ ID NO: 7 (SRTNDYVQDSYP), SEQ ID NO: 8 (SRVTYVQASYP), SEQ ID NO: 9 (HSRTDYVSQTS), SEQ ID NO: 10 (LGDLHNRDNNSA), SEQ ID NO: 11 (GLHTSATNLYLH), SEQ ID NO: 12 (GDGNSVLKPGNW), SEQ ID NO: 13 (TASDVPRSRPHS), SEQ ID NO: 14 (SGVYKVAYDWQH), or variants, or derivatives thereof.

In certain embodiments, the peptides further comprise an alkanoyl amide on the N-terminus, an amide on the C-terminus, fluorescent protein sequence on the N-terminus or C-terminus, polyhistidine on the N-terminus or C-terminus, an amino acid lysine on the N-terminus or C-terminus, an amino acid arginine on the N-terminus or C-terminus, an amino acid aspartic acid on the N-terminus or C-terminus, an amino acid glutamic acid on the N-terminus or C-terminus, an amino acid glutamine on the N-terminus or C-terminus, an amino acid asparagine on the N-terminus or C-terminus, an amino acid histidine on the N-terminus or C-terminus, an amino acid serine on the N-terminus or C-terminus, an amino acid threonine on the N-terminus or C-terminus, an amino acid tyrosine on the N-terminus or C-terminus, an amino acid cysteine on the N-terminus or C-terminus, an amino acid methionine on the N-terminus or C-terminus, an amino acid tryptophan on the N-terminus or C-terminus, an amino acid alanine on the N-terminus or C-terminus, an amino acid isoleucine on the N-terminus or C-terminus, an amino acid leucine on the N-terminus or C-terminus, an amino acid phenylalanine on the N-terminus or C-terminus, an amino acid valine on the N-terminus or C-terminus, an amino acid proline on the N-terminus or C-terminus, an amino acid glycine on the N-terminus or C-terminus, or a heterologous peptide on the N-terminus or C-terminus providing a chimeric peptide. In certain embodiments, the peptides disclosed herein are conjugated to a fatty acid or polyethylene glycol.

In certain embodiments, the peptides disclosed herein are conjugated to a fluorescent label, radioactive label, or a polydentate ligand that binds a metal. In certain embodiments, the peptides disclosed herein are conjugated to a complex of gadolinium. In certain embodiments, the polydentate ligand is diethylenetriamine pentaacetate (DTPA), tetraazacyclododecane-tetraacetate (DOTA), triazacyclononane-triacetic acid (NOTA), or triazacyclononane-phosphinate (TRAP).

In certain embodiments, the peptide disclosed herein have a fluorine label. In certain embodiments, the fluorine is $^{18}F$ (imaging agents for positron emission tomography (PET) or $^{19}F$ (for NMR/MRI). In certain embodiments, the peptides disclosed herein are conjugated to an $Al[^{18}F]$ NOTA-radiotracer, $^{11}C$ labeled 1-$[^{11}C]$-methionine (MET), $^{18}F$ labeled non-natural amino acids: 1-6-$[^{18}F]$fluorodopa (FDOPA), 1-3-$[^{18}F]$-α-methyl-1-tyrosine (FMT), O-(2$[^{18}F]$ fluoroethyl)-1-tyrosine (FET, $[^{18}F]$1), and Anti-1-amino-3-$[^{18}F]$fluorocyclobutyl carboxylic acid (FACBC) on the N-terminus or C-terminus. In certain embodiments the peptide comprises an fluorine or $^{19}F$ containing amino acid such as 4-fluoro-phenylalanine (4F-Phe), 3-fluoro-phenylalanine (3F-Phe), 3-fluoro-tyrosine (3F-Tyr), 4-fluoro-phenylglycine (4F-Phg), 5-fluoro-tryptophan (5F-Trp), and 6-fluoro-tryptophan (6F-Trp) on the N-terminus or C-terminus.

In certain embodiments, the disclosure contemplates detection method comprising: administering an effective amount of a peptide disclosed herein to a subject, e.g., wherein the peptide comprises SEQ ID NO: 1-14, or variants thereof conjugated to a label, and detecting the label in the heart of the subject. In certain embodiments, detecting the label indicates myocarditis because a measured amount of the label correlates to value that is above a reference value indicating the subject has myocarditis.

In certain embodiments, the peptides disclosed herein are conjugated to a drug, anti-viral agent, antibiotic, anti-inflammatory agent, or immunosuppressive agent. In certain embodiments, the drug is a P2X7 receptor antagonist. In certain embodiments, the peptides disclosed herein are conjugated to a dendrimer or exosome. In certain embodiments, the dendrimer or exosome comprises CD40 siRNA or CCR2 siRNA. In certain embodiments, the disclosure relates to methods of treating or preventing heart disease, myocarditis, a slow heard beat, or abnormal heart rhythm comprising administering a peptide conjugated to a drug disclosed herein to a subject in need thereof.

In certain embodiments, this disclose relates to particles comprising peptides disclosed herein. In certain embodiments, the peptide is conjugated to the surface of the particle. In certain embodiments, the particle comprises a core having perfluorocarbons, a water insoluble gas, perfluorocarbon gas, sulfur hexafluoride gas and a shell encapsulating the core comprising lipids, proteins, polymers, or combinations thereof. In certain embodiments, the disclosure contemplates methods of imaging the heart by ultrasound comprising administering particles or microbubbles comprising peptides disclosed herein to a subject and imaging the heart by ultrasound or MRI.

In certain embodiments, the peptides comprise SEQ ID NO: 1-14, or variants thereof. In certain embodiments, the variants have one, two, three, or more amino acid substitutions, insertions, or deletions. In certain embodiments, the peptides are produced synthetically or recombinantly. In certain embodiments, the peptides have at least one non-naturally occurring amino acid substitution, addition, or deletion. In certain embodiments, the amino acid substitutions are conserved substitutions.

In certain embodiments, the disclosure contemplates peptides disclosed herein having at least one molecular modification, e.g., such that the peptide contains a non-naturally amino acid. In certain embodiments, the disclosure contemplates a non-naturally occurring derivative of a peptide having SEQ ID NO: 1-14, variants, or derivatives thereof. In certain embodiments, the disclosure contemplates a derivative in the form of a prodrug. In certain embodiments, the disclosure contemplates a derivative wherein an amino, carboxyl, hydroxyl, or thiol group in a peptide disclosed herein is substituted. In certain embodiments, the disclosure contemplates peptides disclosed herein having a label, e.g., fluorescent or radioactive.

In certain embodiments, the disclosure contemplates a peptide having more than 50%, 60%, 70%, 80%, 90%, 95% sequence identity or similarity to SEQ ID NO: 1-14, and contains at least one substitution and/or modification relative to SEQ ID NO: 1-14 such that the entire peptide is not naturally occurring, e.g., one or more amino acids have been changed relative to the natural sequence.

In certain embodiments, the disclosure relates to recombinant vectors comprising a nucleic acid encoding peptide disclosed herein. In certain embodiments, the disclosure relates to expression systems comprising a recombinant vector comprising a nucleic acid encoding peptide disclosed herein. In certain embodiments, the disclosure relates to cells comprising a recombinant vector comprising a nucleic acid encoding peptide disclosed herein. In certain embodiments, the disclosure relates to a vector comprising the nucleic acid encoding a peptide disclosed herein and a heterologous nucleic acid sequence.

In certain embodiments, the disclosure relates to a nucleic acid encoding a polypeptide disclosed herein wherein the nucleotide sequence has been changed to contain at least one non-naturally occurring substitution and/or modification relative to the naturally occurring sequence, e.g., one or more nucleotides have been changed relative to the natural sequence. In certain embodiments, the disclosure relates to a nucleic acid encoding a polypeptide disclosed herein further comprising a label.

In certain embodiments, the disclosure relates to pharmaceutical compositions comprising a peptide having SEQ ID NO: 1-14, variants, or derivatives thereof and a pharmaceutically acceptable excipient. In certain embodiments, the pharmaceutical composition is in the form of a capsule, tablets, pill, powder, granule, or gel. In certain embodiments, the pharmaceutical composition is in the form of a sterilized pH buffered aqueous salt solution, or in the form of a container configured to spray a liquid, or in the form of a sealed container with a propellant. In certain embodiments, the disclosure contemplates the preparation of a medicament disclosed herein for useful for diagnosing myocarditis or treating or preventing a slowing heartbeat or abnormal heart rhythm. In certain embodiments, the pharmaceutical compositions is in solid form surrounded by an enteric coating. In certain embodiments, the pharmaceutical compositions a pharmaceutically acceptable excipient is a solubilizing agent.

BRIEF DESCRIPTION OF THE DRAWINGS

FIG. 3 data on the quantification of S-MyH-PhD-05 in the heart at 21 days after initial immunization. The ex vivo fluorescent signal in the hearts of animals treated with an IV injection of S-MyH-PhD-05 at 21 days after initial immunization was quantified for the whole heart and for three different sections of the heart: the base, the midsection, and the apex. Fold change relative to spleen. Median values (horizontal line), 25% to 75% percentiles (box), and range of values (whiskers). Control: n=7; No Myocarditis: n=13; Mild Myocarditis: n=16; Severe Myocarditis: n=7.

FIG. 4A shows a sequence comparison of a peptide that targets myocarditis and a BLAST sequence search result of NCBI Accession version WP_020461938.1.

FIG. 4B shows a sequence comparison of a peptide that targets myocarditis and a BLAST sequence search result of NCBI Accession version ESS08305.1.

FIG. 4C shows a sequence comparison of a peptide that targets myocarditis and a BLAST sequence search result of NCBI Accession version GAU36176.1

DETAILED DESCRIPTION

Figures 1, 2:
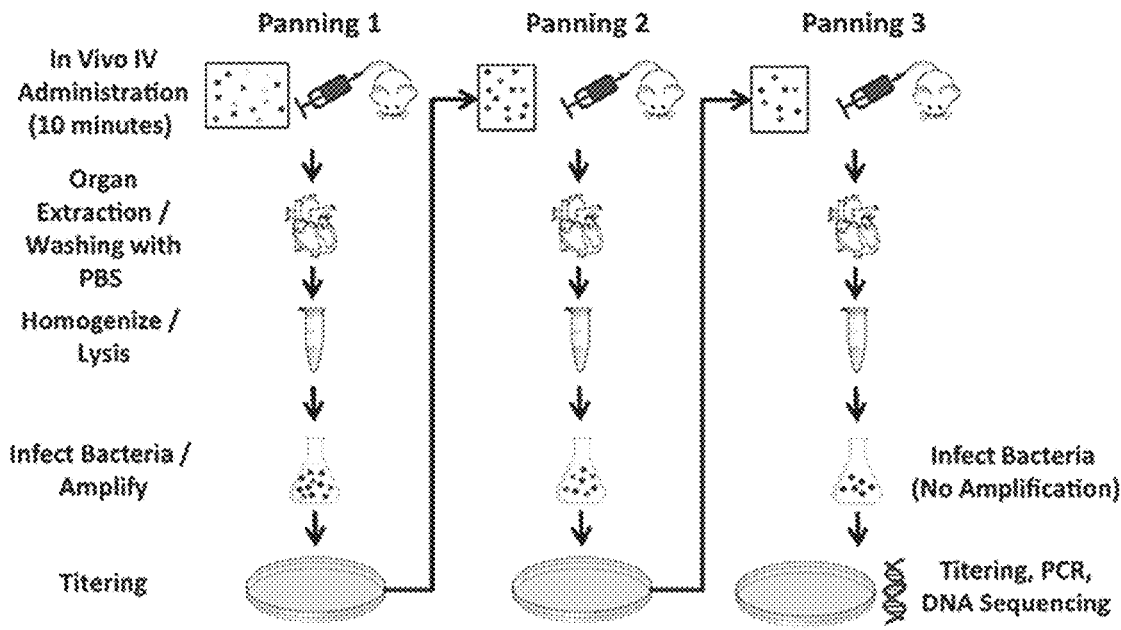
FIG. 1 shows a schematic of in vivo phage display.
FIG. 2 shows a table of sequences for the selected peptides that target myocarditis.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

"Subject" refers any animal, preferably a human patient, livestock, or domestic pet.

The terms "protein" and "peptide" refer to compounds comprising amino acids joined via peptide bonds and are used interchangeably. Amino acids may be naturally or non-naturally occurring. A "chimeric protein" or "fusion protein" is a molecule in which different portions of the protein are derived from different origins such that the entire molecule is not naturally occurring. A chimeric protein may contain amino acid sequences from the same species of different species as long as they are not arranged together in the same way that they exist in a natural state. Examples of a chimeric protein include sequences disclosed herein that are contain one, two or more amino acids attached to the C-terminal or N-terminal end that are not identical to any naturally occurring protein, such as in the case of adding an amino acid containing an amine side chain group, e.g., lysine, an amino acid containing a carboxylic acid side chain group such as aspartic acid or glutamic acid, a polyhistidine tag, e.g. typically four or more histidine amino acids. Contemplated chimeric proteins include those with self-cleaving peptides such as P2A-GSG. See Wang. Scientific Reports 5, Article number: 16273 (2015).

A "variant" refers to a chemically similar sequence because of amino acid changes or chemical derivative thereof. In certain embodiments, a variant contains one, two, or more amino acid deletions or substitutions. In certain embodiments, the substitutions are conserved substitutions. In certain embodiments, a variant contains one, two, or ten or more an amino acid additions. The variant may be substituted with one or more chemical substituents.

One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Certain variants have less than 10%, and preferably less than 5%, and still more preferably less than 2% changes (whether substitutions, deletions, and so on).

As used herein, the term "derivative" refers to a structurally similar peptide that retains sufficient functional attributes of the identified analogue. The derivative may be structurally similar because it is lacking one or more atoms, e.g., replacing an amino group, hydroxyl, or thiol group with a hydrogen, substituted, a salt, in different hydration/oxidation states, or because one or more atoms within the molecule are switched, such as, but not limited to, replacing a oxygen atom with a sulfur atom or replacing an amino group with a hydroxyl group. The derivative may be a prodrug, comprise a lipid, polyethylene glycol, saccharide, polysaccharide. A derivative may be two or more peptides linked together by a linking group. It is contemplated that the linking group may be biodegradable. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

In certain embodiments, the peptides discloses herein have at least one non-naturally occurring molecular modification, such as the attachment of polyethylene glycol, the attachment of a chimeric peptide, the attachment of a fluorescent dye comprising aromatic groups, fluorescent peptide, a chelating agent capable of binding a radionuclide such as $^{18}F$, N-terminal acetyl, propionyl group, myristoyl and palmitoyl, group or N-terminal methylation, or a C-terminal alkyl ester. In certain embodiments, the disclosure contemplates the disclosure contemplates peptides disclosed herein labeled using commercially available biotinylation reagents. Biotinylated peptide can be used in streptavidin affinity binding, purification, and detection. In certain embodiments, the disclosure contemplates peptide disclose herein containing azide-derivatives of naturally occurring monosaccharides such as N-azidoacetylglucosamine, N-azidoacetylmannosamine, and N-azidoacetylgalactosamine.

In certain embodiments, this disclosure contemplates derivatives of peptide disclose herein wherein one or more amino acids are substituted with chemical groups to improve pharmacokinetic properties such as solubility and serum half-life, optionally connected through a linker. In certain embodiments, such a derivative may be a prodrug wherein the substituent or linker is biodegradable, or the substituent or linker is not biodegradable. In certain embodiments, contemplated substituents include a saccharide, polysaccharide, acetyl, fatty acid, lipid, and/or polyethylene glycol. The substituent may be covalently bonded through the formation of amide bonds on the C-terminus or N-terminus of the peptide optionally connected through a linker. In certain embodiments, it is contemplated that the substituent may be covalently bonded through an amino acid within the peptide, e.g. through an amine side chain group such as lysine or an amino acid containing a carboxylic acid side chain group such as aspartic acid or glutamic acid, within the peptide comprising a sequence disclosed herein. In certain embodiments, it is contemplated that the substituent may be covalently bonded through a cysteine in a sequence disclosed herein optionally connected through a linker. In certain embodiments, a substituent is connected through a linker that forms a disulfide with a cysteine amino acid side group.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa,—SORa, —S(=O)$_2$Ra, —OS(=O)$_2$Ra and —S(=O)$_2$ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl. The substituents may further optionally be substituted.

As used herein, the term "dendrimer" or "arborol" can be used interchangeably to refer to compounds with repeating molecular arrangements having branches, e.g., a carbon substituted with at least three substituents, which is typically the result of synthesis from a core molecule. The synthesis may be in two or more directions. The dendrimer product can result in 1 to 2 branching patterns or 1 to 3 branching patterns or 1 to 1 and 2 branching patters as illustrated in Newkome & Shreiner, Dendrimers Derived from 1 [to] 3 Branching Motifs, Chem. Rev. 2010, 110, 6338-6442. See also Mekelburger et al., (1992), Dendrimers, Arborols, and Cascade Molecules: Breakthrough into Generations of New Materials. Angew. Chem. Int. Ed. Engl., 31: 1571-1576.

Hernandez et al. report synthesis of N-[tris(hydroxymethyl)methyl]benzene-carboxamides. J Org Chem, 64, 6905-6906 (1999). The branched molecule, N,N',N"-tris[tris(hydroxymethyl)methyl]-1,3,5-benzenetricarboxamide, as illustrated in FIG. 1, has repeating molecular arrangements represented by branched carbons with hydroxymethyl groups that emanate from a central phenyl ring; thus, N,N',N"-tris[tris(hydroxymethyl)methyl]-1,3,5-benzenetricarboxamide is a dendrimer. In certain embodiments, the hydroxy-terminated dendrimer comprises terminal 1,1-tris (hydroxymethyl)methyl or 1,1,1-tris(hydroxyalkyl)methyl groups.

As used herein, a "lipid" group refers to a hydrophobic group that is naturally or non-naturally occurring that is highly insoluble in water. As used herein a lipid group is considered highly insoluble in water when the point of connection on the lipid is replaced with a hydrogen and the resulting compound has a solubility of less than $0.63 \times 10^{-4}$% w/w (at 25° C.) in water, which is the percent solubility of octane in water by weight. See Solvent Recovery Handbook, $2^{nd}$ Ed, Smallwood, 2002 by Blackwell Science, page 195. Examples of naturally occurring lipids include saturated or unsaturated hydrocarbon chains found in fatty acids, glycerolipids, cholesterol, steroids, polyketides, and derivatives. Non-naturally occurring lipids include derivatives of naturally occurring lipids, acrylic polymers, aromatic, and alkylated compounds and derivatives thereof.

The term "prodrug" refers to an agent that is converted into a biologically active form in vivo. Prodrugs are often useful because, in some situations, they may be easier to administer than the parent compound. The prodrug may also have improved solubility in pharmaceutical compositions over the parent drug. A prodrug may be converted into the parent drug by various mechanisms, including enzymatic processes and metabolic hydrolysis. Typical prodrugs are pharmaceutically acceptable esters. Prodrugs include compounds wherein a hydroxy, amino or mercapto (thiol) group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

For example, if a disclosed peptide or a pharmaceutically acceptable form of the peptide contains a carboxylic acid functional group, a prodrug can comprise a pharmaceutically acceptable ester formed by the replacement of the hydrogen atom of the acid group with a group such as ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as b eta-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

If a disclosed peptide or a pharmaceutically acceptable form of the peptide contains an alcohol functional group, a prodrug can be formed by the replacement of the hydrogen atom of the alcohol group with a group such as ($C_1$-$C_6$) alkanoyloxymethyl, 1-(($C_1$-$C_6$)alkanoyloxy)ethyl, 1-methyl-1(($C_1$-$C_6$)alkanoyloxy)ethyl($C_1$-$C_6$)alkoxycarbonyloxymethyl, N—($C_1$-$C_6$)alkoxycarbonylaminomethyl, succinoyl, ($C_1$-$C_6$)alkanoyl, alpha-amino($C_1$-$C_4$)alkanoyl, arylacyl and alpha-aminoacyl, or alpha-aminoacyl-alpha-aminoacyl, where each alpha-aminoacyl group is independently selected from naturally occurring L-amino acids, P(O)(OH)$_2$, —P(O)(O(C$_1$-C$_6$)alkyl)$_2$, and glycosyl (the radical resulting from the removal of a hydroxyl group of the hemiacetal form of a carbohydrate).

If a disclosed peptide or a pharmaceutically acceptable form of the peptide incorporates an amine functional group, a prodrug can be formed by the replacement of a hydrogen atom in the amine group with a group such as R-carbonyl, RO-carbonyl, NRR'-carbonyl where R and R' are each independently (C$_1$-C$_{10}$)alkyl, (C$_3$-C$_7$)cycloalkyl, benzyl, a natural alpha-aminoacyl, —C(OH)C(O)OY$_1$ wherein Y$^1$ is H, (C$_1$-C$_6$)alkyl or benzyl, —C(OY$_2$)Y$_3$ wherein Y$_2$ is (C$_1$-C$_4$) alkyl and Y$_3$ is (C$_1$-C$_6$)alkyl, carboxy(C$_1$-C$_6$)alkyl, amino(C$_1$-C$_4$)alkyl or mono-Nor di-N,N—(C$_1$-C$_6$)alkylaminoalkyl, —C(Y$_4$)Y$_5$ wherein Y$_4$ is H or methyl and Y$_5$ is mono-N— or di-N,N—(C$_1$-C$_6$)alkylamino, morpholino, piperidin-1-yl or pyrrolidin-1-yl.

As used herein, "pharmaceutically acceptable esters" include, but are not limited to, alkyl, alkenyl, alkynyl, aryl, arylalkyl, and cycloalkyl esters of acidic groups, including, but not limited to, carboxylic acids, phosphoric acids, phosphinic acids, sulfonic acids, sulfinic acids, and boronic acids.

As used herein, "pharmaceutically acceptable enol ethers" include, but are not limited to, derivatives of formula —C=C(OR) where R can be selected from alkyl, alkenyl, alkynyl, aryl, aralkyl, and cycloalkyl. Pharmaceutically acceptable enol esters include, but are not limited to, derivatives of formula —C=C(OC(O)R) where R can be selected from hydrogen, alkyl, alkenyl, alkynyl, aryl, aralkyl, and cycloalkyl.

A "linking group" refers to any variety of molecular arrangements that can be used to bridge to molecular moieties together. An example formula may be —R$_m$—wherein R is selected individually and independently at each occurrence as: —CR$_m$R$_m$—, —CHR$_m$—, —CH—, —C—, —CH$_2$—, —C(OH)R$_m$, —C(OH)(OH)—, —C(OH)H, —C(Hal)R$_m$—, —C(Hal)(Hal)-, —C(Hal)H—, —C(N$_3$)R$_m$—, —C(CN)R$_m$—, —C(CN)(CN)—, —C(CN)H—, —C(N$_3$)(N$_3$)—, —C(N$_3$)H—, —O—, —S—, —N—, —NH—, —NR$_m$—, —(C=O)—, —(C=NH)—, —(C=S)—, —(C=CH$_2$)—, which may contain single, double, or triple bonds individually and independently between the R groups. If an R is branched with an R$_m$ it may be terminated with a group such as —CH$_3$, —H, —CH=CH$_2$, —CCH, —OH, —SH, —NH$_2$, —N$_3$, —CN, or -Hal, or two branched Rs may form a cyclic structure. It is contemplated that in certain instances, the total Rs or "m" may be less than 100, or 50, or 25, or 10. Examples of linking groups include bridging alkyl groups and alkoxyalkyl groups. Linking groups may be substituted with one or more substituents.

As used herein, the term "biodegradable" in reference to a substituent or linker refers to a molecular arrangement in a peptide derivative that when administered to a subject, e.g., human, will be broken down by biological mechanism such that a metabolite will be formed and the molecular arrangement will not persist for over a long period of time, e.g., the molecular arrangement will be broken down by the body after a several hours or days. In certain embodiments, the disclosure contemplates that the biodegradable linker or substituent will not exist after a week or a month.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "sterilized" refers to subjecting something to a process that effectively kills or eliminates transmissible agents (such as fungi, bacteria, viruses, prions and spore forms etc.). Sterilization can be achieved through application of heat, chemicals, irradiation, high pressure or filtration. One process involves water prepared by distillation and stored in an airtight container wherein suitable additives are introduced to approximate isotonicity.

The term "polynucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The polynucleotide may be generated in any manner, including chemical synthesis, DNA replication, reverse transcription, or a combination thereof. The term "oligonucleotide" generally refers to a short length of single-stranded polynucleotide chain usually less than 30 nucleotides long, although it may also be used interchangeably with the term "polynucleotide."

The term "nucleic acid" refers to a polymer of nucleotides, or a polynucleotide, as described above. The term is used to designate a single molecule, or a collection of molecules. Nucleic acids may be single stranded or double stranded, and may include coding regions and regions of various control elements.

A "heterologous" nucleic acid sequence or peptide sequence refers to a nucleic acid sequence or peptide sequence that do not naturally occur, e.g., because the whole sequences contain a segment from other plants, bacteria, viruses, other organisms, or joinder of two sequences that occur the same organism but are joined together in a manner that does not naturally occur in the same organism or any natural state.

The term "recombinant" when made in reference to a nucleic acid molecule refers to a nucleic acid molecule which is comprised of segments of nucleic acid joined together by means of molecular biological techniques provided that the entire nucleic acid sequence does not occurring in nature, i.e., there is at least one mutation in the overall sequence such that the entire sequence is not naturally occurring even though separately segments may occurring in nature. The segments may be joined in an altered arrangement such that the entire nucleic acid sequence from start to finish does not naturally occur. The term "recombinant" when made in reference to a protein or a polypeptide refers to a protein molecule that is expressed using a recombinant nucleic acid molecule.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Proteins may be recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme that confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: amp$^r$, cam$^r$, tet$^r$, blasticidin$^r$, neo$^r$, hyg$^r$, abx$^r$, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferaseI (galT), feedback-insensitive α subunit of anthranilate synthase (OASA1D), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}$S or $^{131}$I) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms or linkers of various lengths to reduce potential steric hindrance.

In certain embodiments, the disclosure relates to recombinant polypeptides comprising sequences disclosed herein or variants or fusions thereof wherein the amino terminal end or the carbon terminal end of the amino acid sequence are optionally attached to a heterologous amino acid sequence, label, or reporter molecule.

In certain embodiments, the disclosure relates to the recombinant vectors comprising a nucleic acid encoding a polypeptide disclosed herein or chimeric protein thereof.

In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory regulatory element (WPRE), scaffold-attachment region (SAR), inverted terminal repeats (ITR), FLAG tag coding region, c-myc tag coding region, metal affinity tag coding region, streptavidin binding peptide tag coding region, poly-His tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic-A V I L; Charged positive: R K H; Charged negative—D E; Polar—S T N Q.

Targeting Peptides for the Diagnosis of Myocarditis

Myocarditis is one of the most challenging diagnosis in cardiology. The gold standard for diagnosis, endomyocardial biopsy (EMB), is invasive and has a high risk for serious complications. Thus, there is a need for noninvasive imaging modalities such as cardiovascular magnetic resonance imaging (CMR), echocardiography, PET, and computerized tomography.

Targeted molecular imaging using fluoride-19 in CMR and antibody coated microbubbles in echocardiography has shown improvements in the diagnosis of myocarditis. However, fluoride-19 is not specific to myocarditis and can be incorporated by macrophages and monocytes in other disease processes such as pneumonia, allograft rejection, cardiac ischemia, and cerebral ischemia.

To address these potential limitations, in vivo phage display was used to identify potential targeting peptides for the diagnosis of myocarditis. Pannings were performed and 36 unique 12 AA peptides were identified. Six of those peptides were selected for ex vivo peptide screening experiments. After ex vivo screening, two peptides, MyH-PhD-05 and MyH-PhD-120, were selected for in vivo peptide screening. Fluorescent imaging after IV delivery of these two peptides demonstrated that MyH-PhD-05 was able to target animals with severe myocarditis in the absence of any functional changes.

The animal model of experimental autoimmune myocarditis (EAM) is efficient in inducing myocarditis in 40-60% of animals immunized. Animals were immunized with MyH/CFA before treatment with S-MyH-PhD-05. All scoring was conducted and analyzed by investigators blinded to the animal's treatment group. Despite the fact that some animals had severe myocarditis as determined by biopsy, functional differences in cardiac function at 21 days were not apparent. This is important as it indicates that the peptide MyH-PhD-05 is able to detect myocarditis in the absence of functional changes.

In vivo phage display was used to identify and test targeting peptides for myocarditis. MyH-PhD-05 targets severe myocarditis. For clinical applications, MyH-PhD-05 can be conjugated to other imaging agents to improve current diagnostic and therapeutic technologies. For example, MyH-PhD-05 can be conjugated to microbubbles for echocardiography or to gadolinium contrast agents for CMR. MyH-PhD-05 can also be conjugated to different dendrimers or exosomes in order to deliver novel therapies such as CD40 siRNA, CCR2 siRNA, or P2X7 receptor antagonist.

Targeted Perfluorocarbon Particles Coated with Peptide Disclosed Herein

In certain embodiments, this disclosure contemplates targeting peptides disclosed herein used on the surface of perfluorocarbons containing particles or microbubbles. Microbubbles, typically 1 to 50 micrometers in diameter or 2 to 8 micrometers in diameter, and contain inner compartment filled by a gas encapsulated in a shell. The shells are typically made of phospholipids, surfactant, and a protein or synthetic polymer. Peptides can be incorporated into the shell surface of microbubbles. Microbubbles provide a reflective interface and resonate to ultrasound waves. They are used as ultrasound contrast agents in imaging, and for drug and gene delivery. In certain embodiments, microbubbles have a shell comprising albumin, albumin and avidin, sorbitan monopalmitate and polyethyoxylated sorbitan monopalmitate, sucrose stearate (mono- and di-ester), phospholipids, saturated diacyl phospholipids, phosphatidyl choline, alginate, biodegradable copolymer f poly(lactide-co-glycolide) (PLGA), poly(vinyl alcohol), copolymer polyperfluorooctyloxycaronyl-poly(lactic acid) (PLA-PFO), and polyelectrolyte multilayer (PEM) e.g. poly(allylamine hydrochloride) (PAH) and poly(styrene sulfonate) (PSS), trimethylammonium propane (TAP) as the underlying shell and DNA and poly(L-lysine) (PLL).

For targeted microbubbles, one can prepare biotinylated microbubbles using appropriately modified procedures reported in Weller et al. Ann Biomed Eng. 2002, 30(8):1012-9. One sonicates of an aqueous dispersion of decafluorobutane gas, phosphatidylcholine, polyethyleneglycol-(PEG-) stearate, and phosphatidylethanolamine-biotin in a 2:1:1 ratio by weight. Microbubbles are combined with streptavidin, washed, and conjugated with biotinylated peptides disclosed herein.

In certain embodiments, ultrasound molecular imaging methods includes one or more of the steps of: (1) injecting intravenously targeted microbubbles having peptide disclosed herein which circulate and adhere to the target tissue, (2) scanning the target tissue is and determining the video intensity (i.e., contrast signal) in the region of interest, e.g. heart tissue, (3) applying a a 'destruction' pulse to fragment and dissolve all microbubbles within the field of view and (4) allowing microbubbles to flow back into the field of view and determining the video intensity in the region of interest, and (5) comparing the signal from targeted microbubbles delineated from that of freely circulating microbubbles and tissue movement by the video intensities before and after the destruction pulse.

Emulsified, biologically inert perfluorocarbons (perfluorocarbon nanoemulsions [PFCs]) are used also used as MM contrast agent. Because 19F is physiologically found in biological tissue in only trace amounts, the resulting fluorine signal displays specificity. Merging of 19F images with corresponding 1H data sets enables the exact anatomic localization of the 19F signal.

In certain embodiments, this disclosure contemplates particles of perfluorocarbon particles comprising peptides disclosed herein. Lecithin is a mixture primarily made up of phospholipids with phosphatidylcholine (PC). Egg or soy lecithin as well as purified phospholipids may be used for pharmaceutical purposes as components of liposomes, mixed micelles, and submicron emulsions. Aqueous lecithin dispersion ((WLD) water lecithin-dispersion) is a system obtained by dispersing lecithin in water or in an isotonic aqueous solution (e.g., mixture of glycerol and water).

Perfluorocarbon nanoemulsions may be prepared using the processes appropriately modified with peptides disclosed herein as outlined in Temme et al. Circulation. 2015, 131: 1405-1414. Egg lecithin may be dispersed in isotonic phosphate buffer with the addition of the perfluoro-15-crown-5 ether. Formed emulsion may be filtered. The N-terminal amine of peptides disclosed herein, or peptides with lysine on the N- or C-terminus of the peptides disclosed herein, may be coupled to Cholesterol-PEG2000-Maleimide to provide a conjugate of the peptide to a cholesterol-PEG anchor. Mixing the emulsion with the conjugate of the peptide to the cholesterol-PEG anchor provides for spontaneous insertion of the cholesterol moiety into the phospholipid layer of the particles of the perfluorocarbon nanoemulsions with the peptide exposed on the exterior of the particle.

Pharmaceutical Methods and Compositions

Methods of administering peptides include, but are not limited to, parenteral administration (e.g., intradermal, intramuscular, intraperitoneal, intravenous and subcutaneous), epidural, and mucosal (e.g., intranasal and oral routes). In a specific embodiment, the peptides or chimeric proteins are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985, 20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903. In a specific embodiment, it may be desirable to administer the pharmaceutical compositions locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. In certain embodiments, the aerosolizing agent or propellant is a hydrofluoroalkane, 1,1,1,2-tetrafluoroethane, 1,1,1,2,3,3,3-heptafluoropropane, propane, n-butane, isobutene, carbon dioxide, air, nitrogen, nitrous oxide, dimethyl ether, trans-1,3,3,3-tetrafluoroprop-1-ene, or combinations thereof.

The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems. For peptides and fusion proteins, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Further, the dosage and frequency of administration of proteins may be reduced by enhancing uptake and tissue penetration of the fusion proteins by modifications such as, for example, lipidation.

The compositions include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. In certain embodiments, the pharmaceutical compositions contain a pharmaceutically acceptable excipient that is a solubilizing agent such as a lipid, cholesterol, fatty acid, fatty acid alkyl ester, linoleic acid, oleic acid arachidonic acid, saccharide, polysaccharide, cyclodextrin, 2-hydoxypropyl(cyclodextrin), or combinations thereof.

In certain embodiments, the pharmaceutical compositions is in solid form surrounded by an enteric coating, i.e., a polymer barrier applied on oral medication that prevents its dissolution or disintegration in the gastric environment. Compounds typically found in enteric coatings include methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, and combinations thereof.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions can be formulated as neutral or salt forms. Pharmaceutically acceptable salts include, but are not limited to, those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

One embodiment provides a pharmaceutical pack or kit comprising one or more containers filled with peptides disclosed herein. Additionally, one or more other prophylactic or therapeutic agents useful for the treatment of a disease can also be included in the pharmaceutical pack or kit. One embodiment provides a pharmaceutical pack or kit including one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration.

In certain embodiment, this disclosure contemplates pharmaceutical compositions comprising proteins disclosed herein and pharmaceutically acceptable excipient. In certain embodiments, this disclosure contemplates the production of a medicament comprising proteins disclosed herein and uses for methods disclosed herein.

In certain embodiments, the disclosure relates to pharmaceutical compositions comprising proteins disclosed herein and a pharmaceutically acceptable excipient. In certain embodiments, the composition is a pill or in a capsule or the composition is an aqueous buffer, e.g., a pH between 6 and 8. In certain embodiments, the pharmaceutically acceptable excipient is selected from a filler, glidant, binder, disintegrant, lubricant, and saccharide.

Compositions suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents solvents or vehicles include water, ethanol, polyols (propylene glycol, polyethylene glycol, glycerol, and the like), suitable mixtures thereof, vegetable (such as olive oil, sesame oil and zuclopenthixol acetate) and injectable organic esters such as ethyl oleate.

Prevention of the action of microorganisms may be controlled by addition of any of various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the proteins may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Liquid dosage forms for oral administration include pharmaceutically acceptable emulsions, solutions, suspensions, syrups, and elixirs. In addition to the proteins, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

In certain embodiments, production processes are contemplated which two components, proteins disclosed herein and a pharmaceutical carrier, are provided already in a combined dry form ready to be reconstituted together. In other embodiments, it is contemplated that proteins disclosed herein and a pharmaceutical carrier are admixed to provide a pharmaceutical composition.

Providing a pharmaceutic composition is possible in a one-step process, simply by adding a suitable pharmaceutically acceptable diluent to the composition in a container. In certain embodiments, the container is preferably a syringe for administering the reconstituted pharmaceutical composition after contact with the diluent. In certain embodiments, the coated proteins can be filled into a syringe, and the syringe can then be closed with the stopper. A diluent is used in an amount to achieve the desired end-concentration. The pharmaceutical composition may contain other useful component, such as ions, buffers, excipients, stabilizers, etc.

A "dry" pharmaceutical composition typically has only a residual content of moisture, which may approximately correspond to the moisture content of comparable commercial products, for example, has about 12% moisture as a dry product. Usually, the dry pharmaceutical composition according to the present invention has a residual moisture content preferably below 10% moisture, more preferred below 5% moisture, especially below 1% moisture. The pharmaceutical composition can also have lower moisture content, e.g. 0.1% or even below. In certain embodiments, the pharmaceutical composition is provided in dry in order to prevent degradation and enable storage stability.

A container can be any container suitable for housing (and storing) pharmaceutically compositions such as syringes, vials, tubes, etc. The pharmaceutical composition may then preferably be applied via specific needles of the syringe or via suitable catheters. A typical diluent comprises water for injection, and NaCl (preferably 50 to 150 mM, especially 110 mM), $CaCl_2$ (preferably 10 to 80 mM, especially 40 mM), sodium acetate (preferably 0 to 50 mM, especially 20 mM) and mannitol (preferably up to 10% w/w, especially 2% w/w). Preferably, the diluent can also include a buffer or buffer system so as to buffer the pH of the reconstituted dry composition, preferably at a pH of 6.2 to 7.5, especially at pH of 6.9 to 7.1.

In certain embodiments, the diluent is provided in a separate container. This can preferably be a syringe. The diluent in the syringe can then easily be applied to the container for reconstitution of the dry compositions. If the container is also a syringe, both syringes can be finished together in a pack. It is therefore preferred to provide the dry compositions in a syringe, which is finished with a diluent syringe with a pharmaceutically acceptable diluent for reconstituting, said dry and stable composition.

In certain embodiments, this disclosure contemplates a kit comprising a pharmaceutical composition disclosed herein and a container with a suitable diluent. Further components of the kit may be instructions for use, administration means, such as syringes, catheters, brushes, etc. (if the compositions are not already provided in the administration means) or other components necessary for use in medical (surgical) practice, such as substitute needles or catheters, extra vials or further wound cover means. In certain embodiments, the kit comprises a syringe housing the dry and stable hemostatic composition and a syringe containing the diluent (or provided to take up the diluent from another diluent container).

EXAMPLES

Peptide Conjugation for In Vivo Delivery

To assess the in vivo targeting potential of peptides identified, either biotinylated MyH-PhD-05 (New England Peptide, MW=1762 g/mol, 1 µg/µL) or biotinylated MyH-PhD-120 (New England Peptide, MW=1791 g/mol, 1 µg/µL), modification was to the N-terminus, were incubated with Streptavidin DyLight 650 (Thermo Fisher Scientific, MW=55,649 g/mol, 1 µg/µL) at a 5:1 molar ratio in PBS for 3 hours at 37° C. in the dark. Using a dialysis unit with a 10 kDa molecular weight cutoff (Microcon Ultracel), the resulting protein was then dialyzed three times for one hour in 500 mL of PBS. Nanodrop 2000c (Thermo Fisher Scientific) was used to determine the final concentration of each compound: (1) S-MyH-PhD-05, and (2) S-MyH-PhD-120.

Ex Vivo Peptide Screening

Animals were used for ex vivo peptide screening in the following treatment groups: (1) untreated controls (n=6); (2) immunized with PBS/CFA (n=9), and (3) immunized with MyH/CFA (n=16). A total of 13 out of 16 animals immunized with MyH/CFA (81.25%) developed myocarditis (Mild: n=8; Severe: n=5). For peptides MyH-PhD-04, MyH-PhD-09, MyH-PhD-13, and MyH-PhD-16, no fluorescent staining was observed on any of the frozen sections of animals for any treatment group (Control, No Myocarditis, Mild Myocarditis, and Severe Myocarditis). These peptides were eliminated from consideration for future experiments.

For peptide MyH-PhD-05, 0 out of 15 animals in the control group, 1 out of 3 animals in the no myocarditis group, 8 out of 8 animals in the mild myocarditis group, and 4 out of 5 animals in the severe myocarditis group were positive for peptide staining (sum score >2). For peptide MyH-PhD-120, 0 out of 15 animals in the control group, 1 out of 3 animals in the no myocarditis group, 3 out of 8 animals in the mild myocarditis group, and 4 out of 5 animals in the severe myocarditis group were positive for peptide staining. Representative images and quantification of the sum score show that staining for peptide MyH-PhD-05 usually corresponds to areas of increased leukocyte infiltration, a similar but a weaker trend was observed in peptide MyH-PhD-120 staining.

To verify that staining was specific to the heart, other off target tissue (lung, liver, spleen, kidney, thigh) in three animals with severe myocarditis were stained with peptide MyH-PhD-05 or MyH-PhD-120. No off target binding of either peptide was observed.

In Vivo Peptide Screening and Echocardiography

Animals were used for ex vivo peptide screening in the following treatment groups: (1) untreated controls (n=8); (2) immunized with PBS/CFA (n=7), and (3) immunized with MyH/CFA (n=48). A total of 29 out 48 animals immunized with MyH/CFA (60.42%) developed myocarditis (Mild: n=20; Severe: n=9). For animals treated with an IV injection of S-MyH-PhD-05 (n=43), the fluorescent signal in the hearts of animals with severe myocarditis (2.05±0.22) was significantly elevated compared to the hearts of animals in the control group (1.38±0.08, p<0.01), animals with no myocarditis (1.42±0.06, p<0.001), and with animals with mild myocarditis (1.52±0.05, p<0.01) as shown in FIG. 3. To determine if this trend was specific to a particular section of the heart, each heart was excised into three different sections (the base, the midsection, and the apex) and imaged. The fluorescent signal in each of the three different sections followed a similar pattern to that observed in the whole heart. To determine if S-MyH-PhD-05 was also targeting other organs, the fluorescent signal in the lung, thigh, liver, and kidney were quantified. No significant differences between treatment groups were observed in any of these organs. In initial studies, a small number of animals were also treated with an IV injection of S-MyH-PhD-120 (n=20). In these animals, the fluorescent signal in the hearts of animals with either mild or severe myocarditis were elevated compared to animals with no myocarditis or in the control group.

Prior to sacrifice, cardiac function was measured in all animals by echocardiography at 21 days post-immunization. There were no changes in any functional parameter measured suggesting detection of myocarditis was prior to onset of dysfunction.

To further show specificity, the ex vivo targeting potential of MyH-PhD-05 in animal model of myocardial infarction (MI) was explored. In this animal model, extensive infiltration of inflammatory cells is expected around 72 hours after MI induction. After allowing the animals to recover for 3 days after permanent ligation of the left anterior descending coronary artery, the animals were euthanized and corresponding sections were then stained with MyH-PhD-05 and imaged. No staining of MyH-PhD-05 was observed in the infarcted tissue.

The invention claimed is:

1. A non-naturally occurring peptide comprising HSRT-DYVQASYP (SEQ ID NO: 6).

2. The peptide of claim 1 further comprising an alkanoyl amide on the N-terminus, an amide on the C-terminus, fluorescent protein sequence on the N-terminus or C-terminus, polyhistidine on the N-terminus or C-terminus, an amino acid lysine on the N-terminus or C-terminus, an amino acid arginine on the N-terminus or C-terminus, an amino acid aspartic acid on the N-terminus or C-terminus, an amino acid glutamic acid on the N-terminus or C-terminus, an amino acid glutamine on the N-terminus or C-terminus, an amino acid asparagine on the N-terminus or C-terminus, an amino acid histidine on the N-terminus or C-terminus, an amino acid serine on the N-terminus or C-terminus, an amino acid threonine on the N-terminus or C-terminus, an amino acid tyrosine on the N-terminus or C-terminus, an amino acid cysteine on the N-terminus or C-terminus, an amino acid methionine on the N-terminus or C-terminus, an amino acid tryptophan on the N-terminus or C-terminus, an amino acid alanine on the N-terminus or C-terminus, an amino acid isoleucine on the N-terminus or C-terminus, an amino acid leucine on the N-terminus or C-terminus, an amino acid phenylalanine on the N-terminus or C-terminus, an amino acid valine on the N-terminus or C-terminus, an amino acid proline on the N-terminus or C-terminus, an amino acid glycine on the N-terminus or C-terminus, or a heterologous peptide on the N-terminus or C-terminus providing a chimeric peptide.

3. The peptide of claim 1 conjugated to a fluorescent label, radioactive label, or a polydentate ligand that binds a metal.

4. The peptide of claim 1 conjugated to a complex of gadolinium.

5. The peptide of claim 1 conjugated to a fatty acid or polyethylene glycol.

6. The peptide of claim 1 conjugated to a drug, anti-viral agent, antibiotic, anti-inflammatory agent, or immunosuppressive agent.

7. A particle comprising a peptide of claim 1.

8. The particle of claim 7 comprising a core having perfluorocarbons, a water insoluble gas, perfluorocarbon gas, or sulfur hexafluoride gas and a shell encapsulating the core comprising lipids, proteins, polymers, or combinations thereof.

9. A method of imaging the heart by ultrasound or MRI comprising administering particles of claim 8 to a subject and imaging the heart by ultrasound or MRI.

10. A recombinant vector comprising a nucleic acid encoding SEQ ID NO:6 in operable combination with a promoter and a heterologous nucleic acid sequence.

11. An expression system comprising a recombinant vector of claim 10.

12. A pharmaceutical composition comprising a peptide having SEQ ID NO: 6 and a pharmaceutically acceptable excipient.

13. The pharmaceutical composition of claim 12 in the form of a sterilized pH buffered aqueous salt solution optionally comprising a saccharide or polysaccharide.

14. The pharmaceutical composition of claim 12 in the form of a capsule, tablets, pill, powder, or granule.

* * * * *